United States Patent [19]

Hinterwaldner et al.

[11] Patent Number: 5,700,455
[45] Date of Patent: Dec. 23, 1997

[54] WATER SOLUBLE, BIODEGRADABLE POLYMERIC MATERIALS FOR SKIN CARE, HAIR CARE AND COSMETIC APPLICATIONS

[75] Inventors: Rudolph Hinterwaldner, Munich, Germany; Helmut H. Weldes, Ocean City, N.J.

[73] Assignee: Permethyl Specialties, L.L.C., Milmay, N.J.

[21] Appl. No.: 711,813

[22] Filed: Sep. 10, 1996

Related U.S. Application Data

[63] Continuation of Ser. No. 349,661, Dec. 5, 1994, abandoned.
[51] Int. Cl.⁶ ................ A61K 7/00; A61K 7/07
[52] U.S. Cl. ................ 424/70.14; 424/401; 514/2; 514/944
[58] Field of Search ................ 424/70.14, 401; 514/2, 944

[56] References Cited

U.S. PATENT DOCUMENTS

| | | |
|---|---|---|
| 3,016,334 | 1/1962 | Lewis . |
| 3,346,408 | 10/1967 | Nakao et al. . |
| 4,186,188 | 1/1980 | Gumprecht et al. . |
| 4,195,077 | 3/1980 | Marsh et al. . |
| 4,451,613 | 5/1984 | Rousseau et al. . |
| 4,474,763 | 10/1984 | Lubowe . |
| 4,504,644 | 3/1985 | Lang et al. . |
| 4,507,279 | 3/1985 | Okuyama et al. . |
| 5,024,742 | 6/1991 | Nesbum et al. . |

FOREIGN PATENT DOCUMENTS

4210334A1 10/1993 Germany .

*Primary Examiner*—Sally Gardner-Lane
*Attorney, Agent, or Firm*—Imre Balogh

[57] ABSTRACT

Water-soluble, biodegradable polymeric materials are provided for skin, hair and cosmetic use comprising the formula:

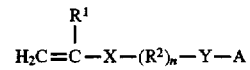

wherein

A is a water soluble, biodegradable polymeric material containing a radical selected from the group consisting of hydroxy, amino, imino, thio and carboxy;

X is

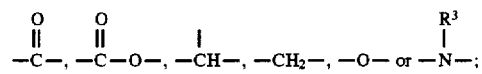

$R^1$ is H, —OH, —CN(=nitrile), halogen or $C_1$–$C_4$ alkyl;

$R^2$ is a saturated or unsaturated, at least bivalent hydrocarbon radical optionally substituted with one or more substituents selected from the group consisting of hydroxy-, amino-, $C_1$–$C_8$ alkyl-, $C_1$–$C_8$ alkoxy- and hydroxyalkyl groups which may be optionally substituted with one or more moieties selected from the group consisting of —CO—, —O—C(O)—O—, —C(O)—O—, —O—, —O—C(O)—, —S—, —NR⁴—, —NH—C(O)— and —NH—C(O)—NH—;

Y is a connecting link to the main chain of the hydrocolloid A selected from the group consisting of —O—, —O—C(O)—, —C(O)—O—, —NH—C(O)— and —C(O)—NH;

$R^3$ and $R^4$ are independently H or alkyl; and n is 0 to 5.

2 Claims, No Drawings

WATER SOLUBLE, BIODEGRADABLE POLYMERIC MATERIALS FOR SKIN CARE, HAIR CARE AND COSMETIC APPLICATIONS

This application is a continuation of application Ser. No. 08/349,661 filed Dec. 5, 1994, now abandoned.

BACKGROUND OF THE INVENTION

1. Field of the Invention

This invention relates to water soluble, biodegradable polymeric materials for skin care, hair care and cosmetic applications. More particularly, the invention relates to hydrocolloids carrying single or multiple ethylenically unsaturated radicals hardened by polymerization incorporated into personal care products.

2. Reported Developments

The skin, hair and nails of the human body comprise collagen and keratin tissues. Environmental influences, such as exposure to ultraviolet radiation, wind, humidity and temperature variation affect this tissue by altering its character by oxidation and physical injuries. To restore the natural qualities of the collagen and/or keratin tissue personal care products have been proposed and marketed in great abundance. Intended for skin care, such compositions include fluid emulsions, lotions, creams and lipstick bases, for example emollient milks or creams for face and hand care, make-up foundations, sunscreen milks and creams and antiperspirant milks or creams. Intended for hair care, such compositions include shampoos, conditioners, rinses, setting lotions, permanent wave agents and sunscreen mousse products. Among the products used to improve the cosmetic feel and appearance of damaged human skin, hair and nails are compositions containing polypeptides. See, for example, U.S. Pat. Nos. 3,016,334; 4,474,763; and 4,507,279.

Polypeptides were also modified and/or derivatized and incorporated in cosmetic compositions to impart certain desirable characteristics to such compositions. See, for example, U.S. Pat. Nos. 4,186,188 and 4,504,644.

It has now been discovered that polypeptides and polysaccharides can be tailor-made for use in personal care products by polymerization with a radical to obtain qualities in such products that are superior to quantities heretofore possessed by personal care products.

SUMMARY OF THE INVENTION

In accordance with the present invention, a water soluble, biodegradable polymeric material is provided comprising the general formula:

$$H_2C=\underset{\underset{R^1}{|}}{C}-X-(R^2)_n-Y-A$$

wherein

A is a water soluble, biodegradable polymeric material containing a radical selected from the group consisting of hydroxy, amino, imino, thio and carboxy;

X is $$-\underset{\underset{}{\overset{\overset{O}{\|}}{}}}{C}-,\ -\underset{\underset{}{\overset{\overset{O}{\|}}{}}}{C}-O-,\ -CH-,\ -CH_2-,\ -O-\ \text{or}\ -\underset{\underset{}{\overset{\overset{R^3}{|}}{}}}{N}-;$$

$R^1$ is H, —OH, —CN(=nitrile), halogen or $C_1$–$C_4$ alkyl;
$R^2$ is a saturated or unsaturated, at least bivalent hydrocarbon radical, which might carry one or several substituents such as hydroxy-, amino-, $C_1$–$C_8$ alkyl-, $C_1$–$C_8$ alkoxy- or hydroxyalkyl groups which, in turn, might carry one or more moieties selected from the group consisting of —CO—, —O—C(O)—O—, —C(O)—O—, —O—, —O—C(O)—, —S—, —NR$^4$—, —NH—C(O)— and —NH—C(O)—NH—;

Y is a connecting link to the main chain of the hydrocolloid A selected from the group consisting of —O—, —O—C(O)—, —C(O)—O—, —NH—C(O)— and —C(O)—NH;

$R^3$ and $R^4$ are independently H or alkyl; and n is 0 to 5.

As used above and throughout this disclosure, the following terms, unless otherwise indicated shall be understood to have the following meanings:

"Alkyl", either alone or with various substituents defined herein, means a saturated aliphatic hydrocarbon, either branched- or straight-chained. Preferred alkyl is "lower-alkyl" having about 1 to about 6 carbon atoms. Examples of alkyl include methyl, ethyl, n-propyl, isopropyl, butyl, sec-butyl, t-butyl, amyl and hexyl.

"Alkoxy" refers to an alkyl-O-group. Preferred alkoxy groups include methoxy, ethoxy, propoxy and butoxy.

The preferred acyloxy group is acetoxy and benzyloxy.

"Halo" means a halogen. Preferred halogens include chloride, bromide and fluoride.

The preferred haloalkyl group is trifluoromethyl.

"Unsaturated bivalent hydrocarbon radical" includes alkenyl and alkynyl groups which may also be branched or straight-chained and preferably contain from 2 to 6 carbon atoms. Such groups include ethenyl, ethynyl, propenyl, allyl, isopropenyl and the like.

Where it appears, alkyl is most preferably $C_1$–$C_4$ alkyl; alkoxy is preferably $C_1$–$C_8$ alkoxy; and the hydrocarbon radical is preferably $C_1$–$C_{10}$ aliphatic hydrocarbon radical containing a moiety selected from the group consisting of —C(O)—O—, —O—C(O)—O—, —O—, —C(O)—, —O—C(O)—, —NH—C(O)— NH—, —N(R$^4$)— or —NH—C(O)—, wherein R$^4$ is H or $C_1$–$C_4$ alkyl.

Still more preferred $R^2$ groups are: bivalent, substituted glycol and polyol radicals having from 2 to 6 carbon atoms; bivalent radicals of a carboxylic acid of $C_2$ to $C_{20}$ glycol ester; and bivalent radicals of a carboxylic acid of $C_6$ to $C_{80}$ polyalkyl glycol ester.

Especially preferred $R^2$ groups are $C_1$ to $C_4$ alkylene radicals which may be substituted with acyloxy, carbonyl, carbonyl dioxy, carbamoyl, hydroximino, imino, ureylene or nitrilo moieties.

n is preferably 0 to 1.

The $R^2$ group is preferably connected to the hydrocolloid A through the connecting link Y, i.e. via ether, ester and/or imino groups, especially —O—, —O—C(O)—O—, —O—C—C(O)—, or NR$^4$ wherein R$^4$ is as defined above.

The connecting link Y between the radical of the general formula $$H_2C=\underset{\underset{R^1}{|}}{C}-X-(R^2)_n-$$

and the main polymer chain of A results from the reaction of the functional groups of the hydrocolloid with the corresponding reactive groups of the above polymerizable radical. Particularly, Y has the same meaning as the hetero groups of radical $R^2$. Especially, $R^1$ is H or CH$_3$;
X is —C(O)—O—, —O—, or —CH$_2$—;
$R^2$ is an aliphatic hydrocarbon radical, preferably a $C_2$ to $C_{10}$ alkylene radical or —(CH$_2$CH$_2$O)$_m$— where m is 1 to 5.

Preferred natural polymeric materials are:
(a) Proteins: such as polypeptides, especially of collagen origin, such as gelatin and animal glues; whey proteins; caseins; plant proteins, especially soy proteins and their hydrolyzates; and
(b) Polysaccharides: such as cellulose and its derivatives such as methyl cellulose, ethyl cellulose, hydroxyethyl cellulose, carboxymethyl cellulose and the like; starch and starch derivatives; glycogen; alginic acid and its derivatives including its salts; agar-agar; hetero-polysaccharides; hetero-glycanes; hemi-celluloses and their derivatives; chitin, gum arabic and guar gum.

Certain specific polymers useful in the practice of the present invention may be characterized as anionic, cationic and neutral polymers.

Examples of anionic polymers include:
(1) sulfated polysaccharides such as: kappa carrageenan lambda carrageenan furcellaren laminarin sulfate galactan sulfate and chondroitin sulfates; and
(2) Carboxylated polysaccharides such as: pecan and algin.

Examples of cationic polymers include: dermatan sulfate keratosulfate hyaluronic acid heparin and chitin.

Examples of neutral polymers include:
(1) Polysaccharides, such as starch, glycogen, glucan, fructans, mannans, galactomannans, glucomannans, galactans, xylans, glycuranans, dextran and starch amylose; and
(2) Cellulose derivatives, such as methylcellulose, hydroxyethylcellulose, ethylhydroxyethylcellulose, hydroxypropyl methylcellulose and hydroxypropylcellulose.

The amounts of the functional radical

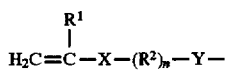

attached to A is preferably of from 0.1 to 90 w/w %, more preferably of from 1 to 50 w/w %, and most preferably of from 3 to 30 w/w %, based on the total w/w % of the formula

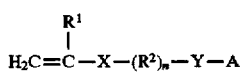

The molecular weight range of the polymeric materials of the present invention is from about 200 to 2,000,000 daltons and preferably from about 500 to 200,000 daltons.

The water soluble biodegradable polymeric materials of the present invention are useful:
(a) In hair treatment products: such as in hair shaping or hair permanents; hair coloring; hair strengthening; and hair care and conditioning;
(b) In skin care products: such as facial creams, masks and sunscreen products;
(c) In cosmetic products: such as lipsticks, lip balms and nail polishes;
(d) In deodorant and/or antiperspirant products;
(e) As carriers: for biologically/cosmetically active materials, such as vitamins, minerals, pH controllers, deodorants and remoisturizing agents; for flavors and fragrances; and
(f) As carriers: for chemicals that affect skin and hair.

DETAILED DESCRIPTION OF THE INVENTION

The present invention is directed to water soluble, biodegradable, natural polymeric materials and their use in personal care, hair care and cosmetic products and as carriers for other materials used in such products. The materials of the present invention (hereinafter sometimes referred to as "functional hydrocolloids") possess properties which are superior to those used for similar applications.

Depending on the molecular weight, the materials of the present invention can be designated as polymerizable or polymeric. Consonant with this designation, the materials can be from totally water soluble to totally water resistant materials. From one aspect, the materials of the present invention can be termed as "functional hydrocolloids", the source or raw materials of which are known and conventional, commercially available hydrocolloids. The chemical modification of these raw materials in producing "functional hydrocolloids" is accomplished by the introduction of reactive and/or functional groups into the main molecular chain of the raw materials without damaging the colloid-chemical and water soluble properties. However, the introduction of these reactive and/or functional groups allows tailor-making the materials suitable for various end uses. The so modified "functional hydrocolloids" of the present invention exhibit properties which show positive effects before, during and after processing, hardening and/or crosslinking. These properties also allow the tailor-making of inert, temperature-resistant, water-resistant and diffusion-resistant polymeric materials useful in skin care, hair care and the like.

The polymeric materials of the present invention are essentially the reaction products of a non-radical reaction between polysaccharides and/or polypeptides in which the hydroxy, amino, imino, thio or carboxylic groups of the polysaccharides or polypeptides are at least partially derivatized by the radical

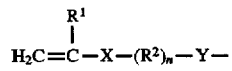

of the general formula

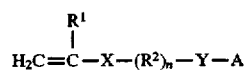

wherein,
A, X, $R^1$, $R^2$ and n are as above-described.

In addition to functionalizing the "functional hydrocolloids" of the present invention by non-radical reaction between the radical and A, derivatization may also be accomplished by graft reactions onto A. However, the so obtained "functional hydrocolloids" show certain disadvantages as compared to the "functional hydrocolloids" prepared by nonradical reaction, such as: the number of graft radicals attached to A may vary and is not easily controlled; it results in the unwanted production of small amounts of homopolymers during the grafting reaction, and its rheological behavior is hard to control.

Accordingly, the "functional hydrocolloids" prepared by the introduction of reactive groups by non-radical reaction onto A is preferred, as well as their preparative method.

Preparation of the functionalized hydrocolloids is carried out as described in German Patent DE-A-42-10-334-A1 and WO 93/20019 which are incorporated herein by reference.

Generalized examples of making the products of the present invention follow.

Polypeptides, such as gelatin and protein hydrolyzaytes

EXAMPLE 1

100 g type B gelatin (bones, 270 bloom) are dissolved in 900 g water at 50° C., the pH is adjusted to 8.5 using 1N NaOH and then, while stirring, 4.45 ml glycidylmethacrylate (GMA) is added and stirring is continued for one hour at 50° C. This GMA amount corresponds to 38 mMol lysin and hydroxylysin per 100 g of gelatin, i.e. a theoretical molar reaction regarding the content of lysin and hydroxylysin. After agitation for one hour at 50° C. the pH is adjusted to 7.0 using 2N $H_2SO_4$. This modified solution can, if desired, be desalted, concentrated, dried or polymerized by standard methods (ion exchange, membrane filtration, spray drying, etc.).

EXAMPLE 2

A 50% solution of collagen hydrolyzate (e.g. "Gelita-Sol" of Deutsche Gelatine-Fabriken Stoess AG) is adjusted to pH 8.5 followed by the addition of 5 wt. % glycidylmethacrylate and stirring for one hour at 50° C. Then the pH is adjusted to 7.0 using 2N $H_2SO_4$. This modified solution can, with or without prior desalting, be dried or polymerized. Polysaccharides, such as corn starch

EXAMPLE 3

600 g corn starch (high amylopectin) content of the type "Amioca AJH-504, National Starch) are suspended in a solution of 120 g $Na_2SO_4$ and 800 ml water. The pH is adjusted to 10.5 to 11.0 using 50% NaOH solution. To obtain a starch degree of substitution of 0.03, i.e. 1% of the free hydroxyl groups of the anhydroglucose units, 13 ml of glycidylmethacrylate are added slowly. After a reaction time of two hours at 50° C. the pH is reduced to 7.0, the starch is removed by a suction filter, washed several times with water and then dried at 40°–45° C. in a circulatory air drying oven.

As earlier described, in the functionalizing of the water soluble, biodegradable polymer materials of the present invention the source materials used are proteins and polysaccharides. The reactive groups

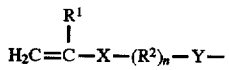

are ethylenically unsaturated and may be attached directly to A at the $H_2C=C$ junction, or they may be attached through a connecting link, e.g. bivalent, or substituted hydrocarbon or polyol radicals. Hardening or polymerization is accomplished by the use of reaction initiators which are customarily used in the prior art, such as by radical-forming hardeners, for example, peroxy compounds, or by irradiation.

The functionalized hydrocolloids of the present invention may contain additional components, such as accelerators, stabilizers, rheology controlling materials, fillers, plasticizers and the like. In addition, the functionalized hydrocolloids of the present invention may be admixed with other polymerizable water soluble and/or water dispersible compounds, such as acrylic and methacrylic compounds.

The hydrocolloids A can be functionalized through one of their several radicals, such as hydroxy, amino, imino, thiol or carboxylic groups. For the functionalization, according to the present invention and as referred to earlier, many unsaturated compounds are suitable, especially compounds carrying acrylic, methacrylic, vinyl and allyl groups. Especially preferred for introduction onto hydrocolloid A are such reactive radicals as acrylic acid glycidyl ester, methacrylic glycidyl ester, acryloxy propionic acid glycidyl ester, methacryloxy propionic acid glycidyl ester, maleic acid monomethyl acryloyloxy ethyl ether, diurethane methacrylate, allyl glycidyl carbonate and methacrylamide.

The polymerization needed for hardening the "functionalized hydrocolloids" can proceed as a straight homopolymerization of a hydrocolloid carrying unsaturated groups according to the generic formula, but it can also take place through the co-polymerization of mixtures of such derivatives. The polymerization or co-polymerization reaction needed for hardening is accomplished by the addition of suitable initiators. Such initiators include: inorganic peroxide-compounds, such as hydrogen peroxide; alkali and/or earth alkali metal peroxide; persulfates and percarbonates; and organic peroxides, such as methyl ethylketone peroxide, cyclohexane peroxide, dibenzoyl peroxide, p-chlorobenzoyl peroxide, acetylacetone peroxide, cumol hydroperoxide and the like.

In addition to the use of initiators in the polymerization and co-polymerization reactions, accelerators may also be used in order to carry out the reaction at a lower temperature. Such accelerators include, for example, triethanolamine and ammonia.

The hardening or crosslinking of the polymeric materials can be carried out continuously or discontinuously. For free radical hardening or crosslinking the initiators are added to the liquid polymeric material and mixed in to attain homogeneity. Depending upon the desired hardening time and temperature, different mounts of initiators and accelerators are used.

The functionalized hydrocolloids of the present invention can also be modified by other additives, such as softening agents, colors, pigments, inorganic and organic fillers and fibers. Stabilizers and inhibitors may also be added.

The hardening or crosslinking of the polymeric materials according to the present invention can be accomplished by irradiation. During hardening or crosslinking with UV irradiation it is necessary to add to the polymeric materials of this invention one or several photosensitive compounds, such as benzoin, and its derivatives, benzyldimethylketales, 1-hydroxycyclohexylphenylketone, benzophenone, 2,4,6-trimethylbenzoil-diphenylphosphine oxide by themselves or in combination with amine-substituted cobalt accelerators, such as Co-2-(dimethylamino) ethylene benzoate. No initiators are needed during hardening or crosslinking by electron beam (EB) initiation. The irradiation dose and duration depends not only upon the contents of reactive groups but also upon the film thickness of the polymeric materials of the invention. Exposure times generally are between 1 to 300 seconds during hardening or crosslinking with UV and EB irradiation. During UV irradiation the UV-A (400 to 320 nm) and UV lamps with an output of 80 to 120 W/cm are preferred. During EB hardening generally an irradiation dose of 5 to 100 kGy are required, preferably 5 to 70 kGy.

In order to obtain storage-stable, moisture and water-resistant gels, coatings or films from the polymeric materials of the present invention it might be necessary to apply dual hardening or crosslinking. As used herein, dual hardening or crosslinking means that various functional groups present on the polymeric material having different reaction mechanisms which will, simultaneously or separately, react with suitable hardeners during the free-radical hardening or crosslinking. An example is the hardening or crosslinking initiated by peroxides and the reaction of —NH— or —OH groups on the polymeric materials with isocyanate groups in one step or two separate steps.

It was found, surprisingly, that through the dual hardening or crosslinking process it is possible to build additional bridge links into or onto the polymeric material which essentially increases water-resistance and decreases swelling without negatively affecting elasticity.

It was also found, surprisingly, that the polymeric materials according to the present invention have, before hardening or crosslinking, the same property, solubility, compatibility and processing characteristics as the un-derivatized basic hydrocolloids; therefore, they can be processed and used in the same way as the basic hydrocolloids. These characteristics are changed only by their homopolymerization or copolymerization with other compounds which contain at least one ethylenically unsaturated double bond.

According to one aspect of the present invention, the polymeric materials of the present invention in colloidal solutions in water are of two kinds:

(a) colloidal water solutions which remain viscous liquids; and (b) colloidal water solutions which exhibit temperature-reversible sol/gel transformation.

Temperature-reversible sol/gel transformation is the phenomenon where a hydrocolloid in aqueous solution exhibits different aggregation, depending on the temperature, and changes from a gel to a sol on heating or cooling. This reversible process can be repeated several times. Typical examples of hydrocolloids which form temperature-reversible gels in their aqueous solution are:

Gelatin, Agar-Agar and Pectins which form gels on cooling; Methylcellulose, such as METHOCEL® which form gels on heating.

The hydrolyzates of the hydrocolloids preferably remain liquid in aqueous solutions according to the present invention. The gels and their hydrolyzates differ in their molecular weights; gels have the higher molecular weights. However, those hydrocolloids which only form concentration-dependent or temperature-dependent viscous solutions, after being functionalized according to the present invention, are interesting and valuable polymeric materials for the preparation of various personal care products. Included in this group are functionalized proteins, gum arabic and guar gum.

Utilizing the Functionalized Hydrocolloids

The functionalized hydrocolloids of the present invention can be homo-polymerized or co-polymerized. The groups for use in the functionalization

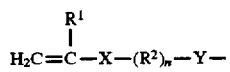

wherein $R^1$, X, $R^2$, Y and n are as previously defined, carry at least one ethylenically unsaturated radical to react with the unmodified natural polymeric material A. The functionalization required for hardening is accomplished through mixing, spraying, dabbing, or brushing application of the reaction initiators needed for the particular system. The type of functionalization and therefore the choice of reaction initiators is largely determined by the intended use of the personal care products that will contain the functionalized hydrocolloids of the present invention. A series of reaction initiators and accelerators used in the process of the present invention are commercially available and approved for use in personal care products.

The physical and/or mechanical properties of the gels, films and coatings, prepared by hardening or crosslinking of the polymeric materials according to this invention, are determined by the molecular weight of the basic, natural hydrocolloids and their hydrolyzates as well as the content of polymerizable radicals of the general formula:

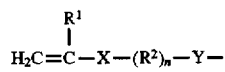

wherein $R^1$, $R^2$, X, Y and n have the meaning previously defined.

Increasing the numbers of radicals of the above general formula increases the number of cross-links as well as the cross-link density in the hardened polymeric materials of this invention which can reduce flexibility and increases brittleness. For low molecular weight hydrocolloids and hydrolyzates comparably greater brittleness is observed already with a low content of these polymerizable radicals. Thus, the physical and/or mechanical properties can be controlled via the molecular weight of the basic hydrocolloids and their hydrolyzates as well as by the number of polymerizable radicals of the above formula.

Surprisingly, it was found that the flexibility of the hardened polymeric materials of this invention can be influenced and modified by the addition of softening agents. Water-soluble and/or water-dispersible polyols and other compounds carrying OH-groups are useful here. Especially such materials are useful, according to this invention, that can be added as active hair and/or skin treatment substances and which are physiologically harmless. These water soluble and/or water dispersible compounds are glycerols, sorbitols, polyols, e.g. polyethylene—and/or polypropylene-glycols, highly branched aliphatic hydrocarbons rich in methyl sidegroups, e.g. PERMETHYL® compounds (Permethyl Corporation, Pottstown, Pa.). Through these softening agents the rehydration and/or the reclimatization of the polymeric materials of this invention can be controlled.

An additional aspect of the invention is the utilization of the multiple property characteristics of the polymeric materials according to this invention, after the hardening or crosslinking process, as personal care products by themselves or as additives to personal care products. Of particular interest are those polymeric materials of this invention which by themselves are useful as skin or hair care products and as skin and hair protection products. Of particular interest are polymeric materials that are based on proteins, especially those based on collagens or keratins. After hardening or crosslinking, these proteins form gels, films and coatings which are resistant to humidity, water and/or other environmental influences and thus are resistant to aging and some of which are long-term biologically active materials.

The polymeric materials of this invention are also useful as additives or auxiliaries for the improvement or modification of the rheological, adhesion, cohesion, wetting and release properties of personal care products.

Additionally, the polymeric materials of this invention are excellent carriers and embedding materials for:

biologically active materials such as vitamins, minerals, pH-controllers, deodorants and remoisturizing agents;

flavors and fragrances; and chemicals that affect skin or hair such as hair-deforming mercaptans, e.g. thioglycolic acid, color-forming and coloring chemicals, bleaches and the like.

After hardening or crosslinking, the polymeric materials of this invention are far superior to the basic hydrocolloids because of their excellent properties described above. Such products include body temperature resistant face masks, deodorant bars and lip balms and lipsticks.

Hair Care Products

Permanents

A major use of the polymeric materials of this invention is in the solidification and hair deformation products. If the polymeric materials are used by themselves in aqueous media then they can be applied to the hair in the same manner as conventional "permanent" hair care products are applied. However, there is a substantial difference in the mechanisms of the hair deformation products of the present invention and that of the conventional hair deformation products: Whereas the aggressive, conventional hair deformation products are applied at pH values of >8.5, the polymeric materials of the present invention can be applied as aqueous hair deformation products in a much less aggressive pH environment, such as at about 6.6 to 8.

The reason for this is as follows: In hair shaping the hydrogen bridges and the disulfide bridges of the keratin have to be split. This splitting is accomplished today by strongly corrosive mercapto-propionic-acid, e.g. thioglycolic acid in an alkaline environment of pH 8–9. To reduce the corrosive properties and to protect the swelled hair some protein hydrolyzates are added today. However, these are almost completely removed during the fixation and rinsing steps. Fixation is accomplished through the application of peroxo compounds, such as $H_2O_2$. However, if the polymeric materials of this invention are used as additives to conventional hair deformation materials on the basis of mercaptan compounds, such as ammoniacal thioglycolic acid, it is not only possible to reduce significantly the content of the aggressive thioglycolic acid but it will also better protect skin and hair from damage. This is especially the case, as was found unexpectedly, for the hair deformation products containing gel-forming polymeric materials of this invention. Similarly, the peroxide-containing fixation solutions which are used with hair deformation products can be improved to be less aggressive to hair and skin by the incorporation of polymeric materials of this invention. The reactive collagen hydrolyzates can also be used alone as a permanent wave former. After applying it to the wet hair strands and putting them on hair curlers, fixation can be accomplished by application of a peroxo solution. In this way permanent waving can be accomplished without the use of the corrosive mercapto acids and at a neutral pH.

Hair Strengthening/Conditioning

When used in hair fixing materials such as hair sprays, the films formed by the polymeric materials of this invention can be hardened or crosslinked with peroxy compounds. The cured and crosslinked films are moisture- and water-resistant.

Hair Coloring

Surprisingly, it was also found that the polymeric materials of this invention, especially those which form gels, are effective additives to hair colorants. In this case the polymeric materials of this invention, besides their skin and hair protective properties, can be used for the permanent fixation of the colorants onto the hair.

Skin Care and Cosmetics

The usefulness of gels in facial masks and the like is very limited with conventional gelling agents such as gelatin and agar-agar. The reason for the limited usefulness of these conventional materials is their reversible sol/gel transformation and the low melting points of such gels. Gelatin gels have a melting point of ≦90° F. (32° C.), i.e. below body temperature. However, if the new reactive gelatin hydrolyzates are used and fixed, the melting point or decomposition point increases to ≧212° F. (100° C.). This allows for the preparation of skin care products on the basis of "natural" materials.

A further characteristic property of the polymeric materials of this invention are their biodegradability after their polymerization, co-polymerization and hardening. Hardened or crosslinked polymers of this invention can be enzymatically biodegraded e.g. in 48 hours and will totally biodegrade in landfills within 200 hours. Thus, crosslinked or non-crosslinked polymers of this invention can be put into any biological landfill and/or waste water systems.

When the polymeric materials of the present invention are incorporated into skin and hair care formulations, certain excipients may be advantageously used in admixtures therewith. Such excipients include surface active agents which may be cationic, anionic and nonionic surface active agents.

Illustrative examples of various formulations follow.

In the examples that follow, the following functionalized hydrocolloids are used.

| Gelatin Hydrolyzate I: | |
| --- | --- |
| Solids content | 60% |
| Molecular Weight ($M_w$) | 3,000 |
| Content of methacrylate groups | ~8 mMol/g dry product |
| Gelatin Hydrolyzate II: | |
| Solids content | 50% |
| Molecular Weight ($M_w$) | 5,000 |
| Content of methacrylate groups | ~16 mMol/g dry product |
| Gelatin Gel I: | |
| Solids content | 20% |
| Molecular Weight ($M_w$) | 60,000 |
| Gel strength @6 2/3% (Bloom) | 200 g |
| Content of methacrylate groups | ~24 mMol/g dry product |
| Gelatin Gel II: | |
| Solids content | 25% |
| Molecular Weight ($M_w$) | 80,000 |
| Gel strength @6 2/3% (Bloom) | 255 g |
| Content of methacrylate groups | ~30 mMol/g dry product |

EXAMPLE 4

| Component A: Hair Deformation Material | |
| --- | --- |
| 10.0 pbw | ammonium thioglycolate (70% aq. solution) |
| 2.0 pbw | gelatin hydrolyzate I |
| 1.5 pbw | ammonium hydrogen carbonate |
| 0.5 pbw | ammonia (28% aq. solution) |
| 0.2 pbw | PERMETHYL ® 101A* |
| 0.1 pbw | perfume oil |
| 85.7 pbw | water |
| | pH 8.2 |
| Component B: Fixation Material | |
| 7.0 pbw | hydrogen peroxide (35% aq. solution) |
| 3.5 pbw | sodium laurylether sulfate |
| 0.1 pbw | citric acid |
| 0.4 pbw | hydroxycetyl hydroxyethyl dimethyl ammonium chloride |
| 0.1 pbw | PERMETHYL ® 102A* |
| 88.9 pbw | water |
| | pH 2.0 |

*A product of The Permethyl Corporation
CTFA - Isohexadecane

Procedure

Medium length, pre-damaged, porous hair is washed with a shampoo, rubbed down and put moist on hair rollers with a diameter of 8 mm. Then the Hair Deformation Material A is distributed uniformly over the rolled-up hair and allowed to remain for 20 minutes. The rolled-up hair is rinsed with water and slightly dried with a towel followed by treatment with Fixation Material B. After 5 minutes the rollers are removed and the hair is rinsed with water. Finally, the hair is slightly rubbed down, formed into the desired hair style and dried.

The finished hair has a soft, smooth feel. It shows excellent wet combability and greatly improved conditioning. The dried hair exhibits a natural, fresh, silky sheen and has a velvety soft feel.

EXAMPLE 5

This was a repetition of Example 1 with the only difference that the Gelatin Hydrolyzate I was omitted form Component A. The thus treated hair had too tight a curl and had a relatively rough feel.

EXAMPLE 6

| Component A: Hair Deformation Material | |
|---|---|
| 8.0 pbw | ammonium thioglycolate (70% aq. solution) |
| 7.5 pbw | gelatin gel II |
| 1.0 pbw | ammonium hydrogen carbonate |
| 0.5 pbw | triethanol amine |
| 0.2 pbw | PERMETHYL ® 101A |
| 0.1 pbw | perfume oil |
| 82.7 pbw | water |
| | pH 8.0 |

Component A is prepared by heating the gelatin gel to 50° to 60° C. As soon as the gel has molten and is completely liquid it is cooled to 40° to 45° C. and the other ingredients are added.

| Component B: Fixation Material | |
|---|---|
| 12.0 pbw | sodium peroxosulfate |
| 3.5 pbw | sodium laurylether sulfate |
| 0.1 pbw | PERMETHYL ® 102A |
| 84.4 pbw | water |

Procedure

Component A, the hair deformation gel is warmed to 38° to 40° C. before application and uniformly distributed to the rolled-up hair at that temperature. Since the material thickens and then gels during cooling, it is more effective on the hair and also protects the scalp considerably better. The procedure continues as in Example 1.

The deformed, wet hair, according to this Example, had a natural velvet-soft curl with excellent spring back characteristics. The dried hair exhibited excellent combability, and a natural, fresh, silky sheen and a good velvety soft feel.

EXAMPLE 7

| Component A: Hair Straightening Gel | |
|---|---|
| 12.5 pbw | ammonium thioglycolate (70% aq. solution) |
| 1.5 pbw | triethanol amine |
| 15.0 pbw | gelatin gel I |
| 2.0 pbw | PERMETHYL ® 101A |
| 1.5 pbw | polyoxyethylene laurylether |
| 67.5 pbw | water |

Preparation as for Component A of Example 6.

| Component B: Fixation Material | |
|---|---|
| 15.0 pbw | sodium peroxysulfate |
| 3.0 pbw | sodium laurylether sulfate |
| 0.2 pbw | PERMETHYL ® 100 EPOXIDE* |
| 81.8 pbw | water |

*A product of The Permethyl Corporation Pentadecane -2,3-epoxide

Procedure

The hair straightening gel (Component A) is heated to 38° to 40° C. to liquify it into a sol before application. This liquid is uniformly applied to the curly, washed and towel-dried hair. The treated hair might also be stretched by the use of hair cups. Afar 15 to 20 minutes the straightened hair is treated several times with the oxidizing fixation material (Component B). This process takes 10 to 15 minutes. Heating with a hair dryer accelerates the fixation process. Finally, the hair is rinsed with water, rubbed down and dried.

The straightened and dried hair had a silky, smooth feel and natural luster.

EXAMPLE 8

| Component A: Permanent Hair Curling Material | |
|---|---|
| 1.0 pbw | sodium laurylether sulfate |
| 6.0 pbw | gelatin hydrolyzate II |
| 4.0 pbw | gelatin gel II |
| 2.0 pbw | mono-ethanolamine |
| 0.5 pbw | ammonium carbonate |
| 2.0 pbw | PERMETHYL ® 101A |
| 84.5 pbw | water |

Preparation as for Component A of Example 6.

| Component B: Fixation Material | |
|---|---|
| 10.0 pbw | sodium peroxosulfate |
| 0.5 pbw | sodium laurylether sulfate |
| 0.5 pbw | PERMETHYL ® 102A |
| 89.0 pbw | water |

Procedure

The washed and towel-dried hair is treated with the permanent hair curling material (Component A) and then put on hair curlers with a diameter of 10 mm. This is followed by treatment of the rolled-up hair with the oxidizing fixation material (Component B) in order to crosslink the reactive methacrylate groups of gelatin hydrolyzate II. After a reaction time of 3 to 5 minutes the curlers are removed, the hair is thoroughly rinsed with water, slightly towel dried, put into the desired hairstyle and then dried. The finished hair had soft curls and exhibited improved conditioning. The permanently curled hair maintained its condition throughout several washes.

EXAMPLE 9

"Sticks"

For the preparation of deodorizing and/or antiperspirant sticks the following composition is used:

| 15.0 to 30.0 pbw | gelatin gel II |
|---|---|
| 1.0 to 5.0 pbw | glycerin or sorbitol |
| 0.1 to 0.5 pbw | triethanol amine |
| 1.0 to 5.0 pbw | PERMETHYL ® 102A |
| 1.0 to 5.0 pbw | isopopylmyristate |
| 0.1 to 0.5 pbw | deodorant or antiperspirant |
| 0.5 to 1.0 pbw | perfume oil |
| 0.5 to 1.0 pbw | sodium peroxosulfate |
| Add 100.0 pbw | water and/or ethanol |

The gelatin gel II is melted in its own water by heating to 40° C. and then the other ingredients are added followed by the additional water and/or ethanol in which the sodium peroxosulfate has been dissolved. The mass is poured into cooled forms and allowed to solidify.

These compositions have excellent esthetics and when applied to the auxiliary area of the user provide effective prevention and control of odor and/or perspiration. They apply smoothly to the skin With an excellent feel and they have very little visible residue.

Through the crosslinking the gel, with its high, toughened rigidity, looses its thermosensitive properties. The gel cannot melt, neither on a human body surface nor when stored at elevated temperatures. This provides for considerably improved retention of active skin care ingredients and/or antiperspirants/deodorants. As a protein-based carrier material the gel itself is a skin care product.

EXAMPLE 10

"Masks"

For the preparation of masks, such as facial skin masks, the following composition was found advantageous:

| 10.0 to 20.0 pbw | gelatin gel I and/or II |
| 5.0 to 10.0 pbw | PERMETHYL ® 101A and/or 102A |
| 0.1 to 1.5 pbw | triethanol amine |
| 0.5 to 1.0 pbw | glycerin monostearate |
| 1.0 to 5.0 pbw | glycerin and/or sorbitol |
| 5.0 to 20.0 pbw | inorganic pigments such as talcum, colloidal aluminum silicate and/or kaolin, borax, magnesium hydroxide, etc. |
| 3.0 to 10.0 pbw | biological additives |
| 0.5 to 1.5 pbw | sodium peroxosulfate |
| Add 100.0 pbw | water |

A facial mask is prepared as follows:

The basic component, without the sodium peroxosulfate, is melted in a water bath at about 50° C. to 60° C. To this melt (sol state) 0.5 to 1.5 pbw sodium peroxosulfate are added and mixed in homogeneously.

The melt is allowed to cool to body temperature and uniformly applied to the face or other body surfaces to be treated.

The coating on the body surface completely solidifies forming, through crosslinking, a gel completely insoluble in water. The active ingredients in the solidified gel can now carry out their function.

The crosslinked gel is not thermo-sensitive and is water resistant and thus can remain on the body surface for longer periods of time. These protein or collagen gels in themselves are especially friendly to the skin.

The gel film on the body surface can easily be removed by peeling or washing with soapy water.

EXAMPLE 11

"Nail Polishes"

A UV-curable nail polish based on products of this invention may have the following composition:

| 10.0 pbw | gelatin hydrolyzate I |
| 10.0 pbw | gelatin gel II |
| 2.0 pbw | glycerin and/or sorbitol |
| 1.0 pbw | PERMETHYL ® 102A |
| 15.0 pbw | isopropanol |
| 4.0 pbw | photoinitiator, e.g. Irgacure 651 (Ciba-Geigy), dissolved in acetone |
| 0.2 pbw | triethanolamine |
| 1.0 pbw | surfactant |
| 5.0 pbw | dye |
| Add 100.0 pbw | water |

The nail polish is applied by brush to the cleaned finger nail surface. It is then crosslinked and hardened by UVA irradiation.

The solidified nail polish based on the gelatin gel has properties very similar to those of human finger nails. The crosslinked gel structure has excellent adhesion to the nail surface. Also, through the inclusion of the plasticizing and humidity controlling glycerin and sorbitol, the solidified nail polish gel conforms—just like the nail itself—much better to the contour of the nail surface without delamination.

The solidified nail polish coating is insoluble in water.

EXAMPLE 12

"Hair Coloring Material"

In order to obtain improvements of semi-permanent and permanent hair coloring products with respect to more pronounced and more durable nuances, 5 wt % of gelatin hydrolyzate I and gelatin gel II were added to standard commercial hair coloring products based on oxidative hair dyes and mixed in homogeneously. Hair colored with these modified material showed, after the oxidative fixing process, greatly improved and more homogeneous shades which remained unchanged even after 10 washings. Hair colored with the products not modified with the reactive protein polymers of this invention showed marked changes in the color nuances already after 4 to 5 washes.

EXAMPLE 13

"Hair Bleaching Gel"

The gel had the following composition:

| 8.0 pbw | hydrogen peroxide (35%) |
| 10.0 pbw | gelatin gel I |
| 2.0 pbw | PERMETHYL ® 101A |
| 5.0 pbw | glycerin monostearate |
| 5.0 pbw | sodium laurylether sulfate |
| 1.0 pbw | citric acid |
| Add 100.0 pbw | water |

Washed, towel-dried, dark hair strands were treated with this hair bleaching gel and left on for 10 minutes. The bleached hair strands were then treated with a 1% aqueous solution of triethanolamine to accelerate the free-radical crosslinking reaction of the methacrylate groups on the protein polymers of this invention. After treatment for 5 minutes, the bleached hair was rinsed thoroughly with water, towel-dried and then heat dried. This dry, bleached hair had a very smooth feel and silky gloss.

Use of the bleaching gel based on these protein-containing, skin-friendly carrier materials, not only protects the scalp but also accelerates the bleaching process under mild, hair-protecting conditions.

After application of the triethanolamine the remaining hydrogen peroxide is quickly destroyed. Through the crosslinked gel the bleached hair carries an effective and protective coating film which is not removed by subsequent washing. The especially sensitive bleached hair is less brittle and rough because of the protective protein coating.

EXAMPLE 14

10.0 pbw corn starch (type Amioca HJH-504, National Starch) with a methacrylic group content of 15 mMol/g was dispersed in 70 pbw water and cooked for 30 minutes at 75° C. Then 2.0 pbw PERMETHYL®102A and 18.0 pbw glycerin were added and mixed in homogeneously. Finally, 0.5 pbw $Na_2S_2O_8$ was added and the mass was poured into a form. After about 10 to 15 minutes the material had solidified and was removed in the form of a stick. These sticks were no longer soluble in water and were even resistant to boiling water.

A variety of active ingredients can be embedded in these sticks.

EXAMPLE 15

The high molecular weight bio-polymers of this invention and used in the preceding examples are easily biodegradable. The crosslinked products in the form of a foil, were incubated with 1 pbw pepsin in 0.1% HCl at 37° C. Depending upon the degree of derivatization and the polymerization conditions, the crosslinked polymers dissolved within 2 to 7 days.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A skin care composition comprising:

(1) of from about 0.1% w/w to about 50.0% w/w of a polymeric material of the formula I:

$$H_2C=C(R^1)-X-(R^2)_n-Y-A \quad\quad I$$

said polymeric material having a molecular weight of from about 500 to about 200,000 daltons,
   wherein A is a water soluble, biodegradable polymeric hydrocolloid containing a radical selected from the group consisting of hydroxy, amino, imino, thio and carboxy; said hydrocolloid is selected from the group consisting of gelatin, whey protein, casein, plant protein, whey protein hydrolyzate, casein hydrolyzate and plant protein hydrolyzate;

X is $$-C(O)-,\ -C(O)-O-,\ -CH_2-,\ -O-\ \text{or}\ -N(R^3)-;$$

$R^1$ is H, —OH, —CN(=nitrile), halogen or $C_1$-$C_4$ alkyl;

$R^2$ is a saturated or unsaturated, at least bivalent hydrocarbon radical optionally substituted with one or more substituents selected from the group consisting of hydroxy-, amino-, $C_1$-$C_8$ alkyl-, $C_1$-$C_8$ alkoxy- and hydroxyalkyl groups which may be optionally substituted with one or more moieties selected from the group consisting of —CO—, —O—C(O)—O—, —C(O)—O—, —O—, —O—C(O)—, —S—, —NR$^4$—, —NH—C(O)—and —NH—C(O)—NH—;

Y is a connecting link to the main chain of the hydrocolloid A selected from the group consisting of —O—, —O—C(O)— and —C(O)—O—;

$R^3$ and $R^4$ are independently H or alkyl; and n is 0 to 5;

2) of from about 0.1% w/w to about 45.0% w/w of a cosmetically acceptable excipient selected from the group consisting of a nonionic surfactant, a cationic surfactant, an anionic surfactant, an emollient, a colorant, a preservative and a perfume; and 3) of from about 49.9% w/w to about 54.9% w/w water.

2. A hair care composition comprising:

(1) of from about 0.5% w/w to about 35.0% w/w of a polymeric material of the formula I $$H_2C=C(R^1)-X-(R^2)_n-Y-A \quad\quad I$$

said polymeric material having a molecular weight of from about 200 to about 2,000,000 daltons, wherein A is a water soluble, biodegradable polymeric hydrocolloid containing a radical selected from the group consisting of hydroxy, amino, imino, thio and carboxy, said hydrocolloid is selected from the group consisting of of gelatin, whey protein, casein, plant protein, whey protein hydrolyzate, casein hydrolyzate and plant protein hydrolyzate;

X is $$-C(O)-,\ -C(O)-O-,\ -CH_2-,\ -O-\ \text{or}\ -N(R^3)-;$$

$R^1$ is H, —OH, —CN(=nitrile), halogen or $C_1$-$C_4$ alkyl;

$R^2$ is a saturated or unsaturated, at least bivalent hydrocarbon radical optionally substituted with one or more substituents selected from the group consisting of hydroxy-, amino-, $C_1$-$C_8$ alkyl-, $C_1$-$C_8$ alkoxy- and hydroxyalkyl groups which may be optionally substituted with one or more moieties selected from the group consisting of —CO—, —O—C(O)—O—, —C(O)—O—, —O—, —O—C(O)—, —S—, —NR$^4$—, —NH—C(O)—and —NH—C(O)—NH—;

Y is a connecting link to the main chain of the hydrocolloid A selected from the group consisting of —O—, —O—C(O)— and —C(O)—O—;

$R^3$ and $R^4$ are independently H or alkyl; and n is 0 to 5;

2) of from about 2.0% w/w to about 35.0% w/w of a cosmetically acceptable excipient selected from the group consisting of a nonionic surfactant, a cationic surfactant, an anionic surfactant, an emollient, a colorant, a preservative and a perfume; and 3) of from about 62.5% w/w to about 64.5% w/w water.

* * * * *